United States Patent
Liu et al.

(10) Patent No.: US 9,624,588 B2
(45) Date of Patent: *Apr. 18, 2017

(54) MULTI-COMPONENT ELUENT GENERATING SYSTEM AND METHOD

(71) Applicant: DIONEX CORPORATION, Sunnyvale, CA (US)

(72) Inventors: Yan Liu, Palo Alto, CA (US); Petr Jandik, Framingham, MA (US); Christopher A. Pohl, Union City, CA (US)

(73) Assignee: Dionex Corporation, Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,357

(22) Filed: Jun. 15, 2015

(65) Prior Publication Data

US 2015/0275380 A1    Oct. 1, 2015

Related U.S. Application Data

(63) Continuation of application No. 13/611,631, filed on Sep. 12, 2012, now Pat. No. 9,086,426.

(51) Int. Cl.
  *C25B 9/18*  (2006.01)
  *C25B 1/02*  (2006.01)
  (Continued)

(52) U.S. Cl.
  CPC ............. *C25B 9/18* (2013.01); *B01D 15/166* (2013.01); *B01D 15/361* (2013.01); *C25B 1/02* (2013.01);
  (Continued)

(58) Field of Classification Search
  CPC .... B01D 15/166; B01D 15/361; B01D 61/44; G01N 30/34; G01N 30/96;
  (Continued)

(56) References Cited

U.S. PATENT DOCUMENTS 3,926,559 A    12/1975  Stevens
6,225,129 B1    5/2001  Liu et al.
(Continued)

FOREIGN PATENT DOCUMENTS

WO    2007092798 A2    8/2007
WO    2011158430 A1    12/2011

OTHER PUBLICATIONS

Balchunas et al, "Gradient Elution for Micellar Electrokinetic Capillary Chromatography," Anal. Chem. 60, 617-621, 1988.
(Continued)

*Primary Examiner* — Daniel S Larkin
(74) *Attorney, Agent, or Firm* — Timothy J. Ohara (57) ABSTRACT

A system and method to generate a concentration gradient eluent flow are described. The concentration gradient eluent flow can include at least two different generants. A liquid can be pumped to an eluent generating device. A first controlling signal can be applied to a first eluent generator to generate a first generant. A second controlling signal can be applied to a second eluent generator to generate a second generant. Either the first and/or the second controlling signal can be varied as a function of time to generate the concentration gradient eluent flow.

17 Claims, 6 Drawing Sheets

(51) Int. Cl.

| | |
|---|---|
| *C25B 3/00* | (2006.01) |
| *C25B 13/00* | (2006.01) |
| *C25B 1/14* | (2006.01) |
| *G01N 30/34* | (2006.01) |
| *G01N 30/16* | (2006.01) |
| *B01D 15/16* | (2006.01) |
| *B01D 15/36* | (2006.01) |
| *G01N 30/96* | (2006.01) |
| *B01D 61/44* | (2006.01) |

(52) U.S. Cl.
CPC .................. *C25B 1/14* (2013.01); *C25B 3/00* (2013.01); *C25B 13/00* (2013.01); *G01N 30/16* (2013.01); *G01N 30/34* (2013.01); *G01N 30/96* (2013.01); *B01D 61/44* (2013.01); *G01N 2030/965* (2013.01); *Y02E 60/34* (2013.01); *Y10T 137/0318* (2015.04)

(58) Field of Classification Search
CPC .... G01N 2030/965; G01N 30/16; C25B 9/18; C25B 1/02; C25B 1/14; C25B 3/00; C25B 13/00; Y10T 137/0318; Y02E 60/34

See application file for complete search history.

(56) References Cited

U.S. PATENT DOCUMENTS

| | | | |
|---|---|---|---|
| 6,544,484 B1 | 4/2003 | Kaufman et al. | |
| 6,568,245 B2 | 5/2003 | Kaufman | |
| 6,682,701 B1 | 1/2004 | Liu et al. | |
| 7,329,346 B2 | 2/2008 | Liu et al. | |
| 7,531,075 B2 | 5/2009 | Anderson, Jr. et al. | |
| 7,767,462 B2 | 8/2010 | Liu et al. | |
| 8,043,507 B2 | 10/2011 | Liu et al. | |
| 8,216,515 B2 | 7/2012 | Liu et al. | |
| 9,086,426 B2 * | 7/2015 | Liu | ...................... B01D 15/166 |
| 2004/0048389 A1 | 3/2004 | Liu et al. | |
| 2004/0214344 A1 | 10/2004 | Anderson, Jr. et al. | |
| 2006/0186046 A1 | 8/2006 | Liu et al. | |
| 2006/0231404 A1 | 10/2006 | Riviello | |
| 2009/0205409 A1 | 8/2009 | Ciavarini et al. | |
| 2009/0218238 A1 | 9/2009 | Dasgupta et al. | |
| 2010/0144051 A1 | 6/2010 | Liu et al. | |
| 2010/0307919 A1 | 12/2010 | Liu et al. | |
| 2012/0024793 A1 | 2/2012 | Liu et al. | |

OTHER PUBLICATIONS

Chien et al., Poster presentation, "Enhanced Speed of Gradient Capillary HPLC Analysis of Compounds of Pharmaceutical Interest by Ultrafast Stationary/Mobile Phase Re-Equilibration," 2004.

GS50 Gradient Pump Operator's Manual, Doc. No. 031612, Rev. 03, Oct. 2003, 162 pages.

Kutter et al., "Integrated Microchip Device with Electrokinetically Controlled Solvent Mixing for Isocratic and Gradient Elution in Micellar Electrokinetic Chromatography," Anal. Chem., 69, 5165-5171, 1997.

Product Manual for EG40 Eluent Generator System, Doc. No. 031373, Rev. 06, Jul. 8, 2002, 54 pages.

Product Manual for Eluent Generator Cartridges, Doc. No. 065018, Rev. 03, Jul. 2011, 63 pages.

Rozing et al., "A System and Columns for Capillary HPLC," American Laboratory, May 2001, 10 pages.

* cited by examiner

MULTI-COMPONENT ELUENT GENERATING SYSTEM AND METHOD

CROSS REFERENCE TO RELATED APPLICATIONS

This application is a Continuation under 35 U.S.C. §120 and claims the priority benefit of U.S. application Ser. No. 13/611,631, filed Sep. 12, 2012, now U.S. Pat. No. 9,086,426, entitled "MULTI-COMPONENT ELUENT GENERATING SYSTEM AND METHOD," which application is hereby incorporated herein by reference in their entireties.

BACKGROUND

Ion chromatography (IC) is a widely used analytical technique for the determination of anionic and cationic analytes in various sample matrices. Typical separation columns for IC have an internal diameter ranging from about 2 to 4 millimeters and are operated at flow rates ranging from 0.2 to 3 mL/min. In an effort to improve the performance of IC, research has been performed to develop separation columns with smaller diameters. Such smaller columns are typically referred to as a capillary separation column when the internal diameter is about 1 millimeter or less.

The use of capillary separation columns has been found to improve the separation efficiency and/or reduce the analysis time. In addition to improved separation performance, capillary IC offers numerous other advantages such as a small sample volume requirement (e.g., 1 microliter or less) and a lower eluent usage. A capillary ion chromatography system typically operates at a flow rate ranging from 1 to 20 microliters/minute, and thus, the amount of eluent consumed is very small. The relatively low eluent usage makes long term continuous operation economically reasonable. For example, the total eluent usage for an entire year may only be about 5 liters using a typical capillary flow rate. A continuously operated always "on" system reduces the number of problems and time associated with system start-up and shutdown. In addition, low flow rates improve the system compatibility with a mass spectrometer. Another advantage of low volume capillary columns is that the required amount of stationary phase resin is relatively low. In turn, this either reduces costs or makes it economically feasible to use more expensive and exotic materials in the column.

In capillary IC, the eluent can be pumped to the capillary column using an isocratic or a concentration gradient eluent delivery mode. In ion chromatography, the eluent typically is an aqueous solution containing acid, or base, or salts. The eluent may also contain some organic solvents. The chemical composition of eluent delivery mode can be selected based on the chemical properties of the analyte, matrix, and capillary column. In the isocratic mode, the composition of the eluent is constant for the duration of the sample analysis. In contrast, the concentration gradient mode provides an eluent composition that changes as a function of time during the sample analysis. For example, the eluent composition can have one or more components such as, for example, an acid, base, or salt where the component concentration changes as a function of time.

In conventional scale IC that uses a 2 to 4 millimeter (internal diameter) separation column, concentration gradient eluent delivery with two or more components is typically performed with a high-pressure pump fitted with a low-pressure proportioning valve. Such a pump can typically be capable of proportioning up to four different eluent components that can each be independently varied as a function of time. The conventional scale concentration gradient pumps can have delay volumes of about 1 mL associated with the pump head and proportioning valve. This delay volume is not compatible with capillary scale IC separations since it corresponds to a delay time of about 100 minutes if the separation flow rate is about 10 microliters/minute. The delay time to change the eluent composition can be about the same or exceed the assay time of a typical capillary IC analysis. Clearly, the delay time must be substantially less than the assay time to have an effective concentration gradient eluent delivery. As such, Applicants believe that there is a need for concentration gradient eluent delivery systems having lower dead volumes than those observed with conventional scale concentration gradient pumps. Applicants also believe that concentration gradient eluent delivery systems with relatively low dead volume will enhance the separation capabilities of capillary chromatography such as, for example, in the analysis of carbohydrates and amino acids, where aqueous multi-component eluents at varying concentrations are typically required.

SUMMARY

A first system that generates a concentration gradient eluent flow for a chromatographic separation is described. The first system includes a pump, an electrolytic eluent generating device, and an electronic circuit. The pump is configured to pump a liquid. The electrolytic eluent generating device is configured to generate at least two different generants where a first generant concentration and a second generant concentration are both controllable as a function of time. The electrolytic eluent generating device includes a first and a second eluent generators. The first eluent generator can be configured to receive the liquid from the pump; add a first generant and a first gas byproduct to the liquid; and output the liquid that includes the first generant and the first gas byproduct. The second eluent generator can be configured to receive the liquid from the first eluent generator; add a second generant and a second gas byproduct to the liquid; and output the liquid that includes the first generant, the second generant, the first gas byproduct, and the second gas byproduct. The electronic circuit can be configured to apply a first controlling signal to the first eluent generator to generate the first generant concentration, and apply a second controlling signal to the second eluent generator to generate the second generant concentration, where at least one of the first or second controlling signals can be increased or decreased as a function of time to generate the concentration gradient eluent flow.

The above first system may also include a catalytic elimination device that contains a catalyst and an inlet configured to receive the liquid from the second eluent generator. The catalyst causes the first gas byproduct and the second gas byproduct to react and form water. The catalytic elimination can also be configured to decompose a hydrogen peroxide byproduct.

A second system that generates a concentration gradient eluent flow for a chromatographic separation is described. The second system includes a pump, an electrolytic eluent generating device, and an electronic circuit. The pump is configured to pump a liquid. The electrolytic eluent generating device can be configured to generate at least two different generants where a first generant concentration and a second generant concentration are both controllable as a function of time. The electrolytic eluent generating device includes a first eluent generator, second eluent generator, and a fluid junction. The first eluent generator can be configured to receive the liquid from the pump; add a first generant and a first gas byproduct to the liquid; and output the liquid that includes the first generant and the first gas byproduct. The second eluent generator can be configured to receive the liquid from the pump; add a second generant and a second gas byproduct to the liquid; and output the liquid that includes the second generant and the second gas byproduct. The fluid junction including a first inlet, a second inlet, and an outlet, where the first inlet is configured to receive the liquid from the first eluent generator; the second inlet is configured to receive the liquid from the second eluent generator; the outlet is configured to flow a mixture of the first generant, the second generant, the first gas byproduct, and the second gas byproduct. The electronic circuit can be configured to apply a first controlling signal to the first eluent generator to generate the first generant concentration, and apply a second controlling signal to the second eluent generator to generate the second generant concentration, where at least one of the first or second controlling signals can be increased or decreased as a function of time to generate the concentration gradient eluent flow.

The above second system may also include a catalytic elimination device that contains a catalyst and an inlet configured to receive the liquid from the fluid junction. The catalyst causes the first gas byproduct and the second gas byproduct to react and form water. The catalytic elimination can also be configured to decompose a hydrogen peroxide byproduct.

The above first or second systems can be configured to interface with a chromatographic separation device that includes a capillary chromatographic separation device.

The electronic circuit of the above first or second systems may also be configured to synchronize with an actuation of the injection valve so that at least a portion of the concentration gradient eluent flow elutes the analyte on the chromatographic separation device. In an embodiment, the first controlling signal and the second controlling signal may include a first current and a second current, respectively. In another embodiment, the first controlling signal and the second controlling signal may include a first voltage and a second voltage, respectively.

The above first or second systems can be configured to have a dead volume ranging from about 1 microliter to about 100 microliters. The first eluent generator includes a first generation chamber that has a first volume. The second eluent generator includes a second generation chamber that has a second volume. The dead volume is a sum of the first volume and the second volume.

The first generant of the above first or second system can be a compound including an anion and a cation, the anion selected from the group consisting of a hydroxide, a carbonate, a phosphate, a sulfate, a trifluoroacetate, an acetate, a methanesulfonate, and a combination thereof, the cation selected from the group consisting of a hydronium, a potassium, a sodium, a lithium, an ammonium, and a combination thereof. The second generant of the above first or second system can be a compound including an anion and a cation, the anion selected from the group consisting of a hydroxide, a carbonate, a phosphate, a sulfate, a trifluoroacetate, an acetate, a methanesulfonate, and a combination thereof, the cation selected from the group consisting of a hydronium, a potassium, a sodium, a lithium, an ammonium, and a combination thereof. In an embodiment, the first generant and the second generant do not share a common anion.

A method of generating a concentration gradient eluent flow is described, that includes at least two different generants, to a chromatographic separation device. The method includes pumping a liquid. Next, a first controlling signal can be applied to a first eluent generator to generate a first generant concentration. A first generant and a first gas byproduct can be generated with the first eluent generator. The first generant and the first gas byproduct can be added to the liquid. A second controlling signal can be applied to a second eluent generator to generate a second generant concentration. A second generant and a second gas byproduct can be generated with the second eluent generator. The second generant and the second gas byproduct can be added to the liquid. At least one of the first or the second controlling signal can be increased as a function of time to generate the concentration gradient eluent flow. In another embodiment, at least one of the first or the second controlling signal can be decreased as a function of time to generate the concentration gradient eluent flow.

The method may also include injecting a liquid sample that includes an analyte or a number of analytes into a chromatographic separation device; inputting the liquid that includes the first generant and the second generant to provide a concentration gradient eluent flow into the chromatographic separation device; separating the analyte from matrix components and separating the analytes from each other in the chromatographic separation device; and detecting the analyte with a detector. In addition, the method may also include synchronizing an actuation of the injection valve with the first or second controlling signal so that at least a portion of the concentration gradient eluent flow elutes the analyte on the chromatographic separation device. The method may also include forming water in a catalytic elimination device by a reaction of the first gas byproduct and the second gas byproduct. In an embodiment, the first controlling signal and the second controlling signal may include a first current and a second current, respectively. In another embodiment, the first controlling signal and the second controlling signal may include a first voltage and a second voltage, respectively.

In an embodiment to the method described above, the adding of the second generant is to a liquid that already contains the first generant.

In another embodiment to the method described above, the first controlling signal is approximately constant as a function of time and the second controlling signal increases approximately linearly as a function of time. The first generant can include a hydroxide anion and the second generant can include a methanesulfonic acid. Whereby, the concentration gradient includes a decreasing concentration gradient of the hydroxide anion and an increasing concentration gradient of methanesulfonate.

BRIEF DESCRIPTION OF THE DRAWINGS

The accompanying drawings, which are incorporated herein and constitute part of this specification, illustrate presently preferred embodiments of the invention, and, together with the general description given above and the detailed description given below, serve to explain features of the invention (wherein like numerals represent like elements).

DETAILED DESCRIPTION OF EMBODIMENTS

The following detailed description should be read with reference to the drawings, in which like elements in different drawings are identically numbered. The drawings, which are not necessarily to scale, depict selected embodiments and are not intended to limit the scope of the invention. The detailed description illustrates by way of example, not by way of limitation, the principles of the invention. This description will clearly enable one skilled in the art to make and use the invention, and describes several embodiments, adaptations, variations, alternatives and uses of the invention, including what is presently believed to be the best mode of carrying out the invention. As used herein, the terms "about" or "approximately" for any numerical values or ranges indicate a suitable dimensional tolerance that allows the part or collection of components to function for its intended purpose as described herein.

A concentration gradient eluent delivery apparatus will be described that is configured to pump multi-component eluents to a capillary separation column. The concentration gradient eluent delivery apparatus is typically a portion of a chromatography system that analyses anions, cations, or other target analytes of a sample.

Figure 1:
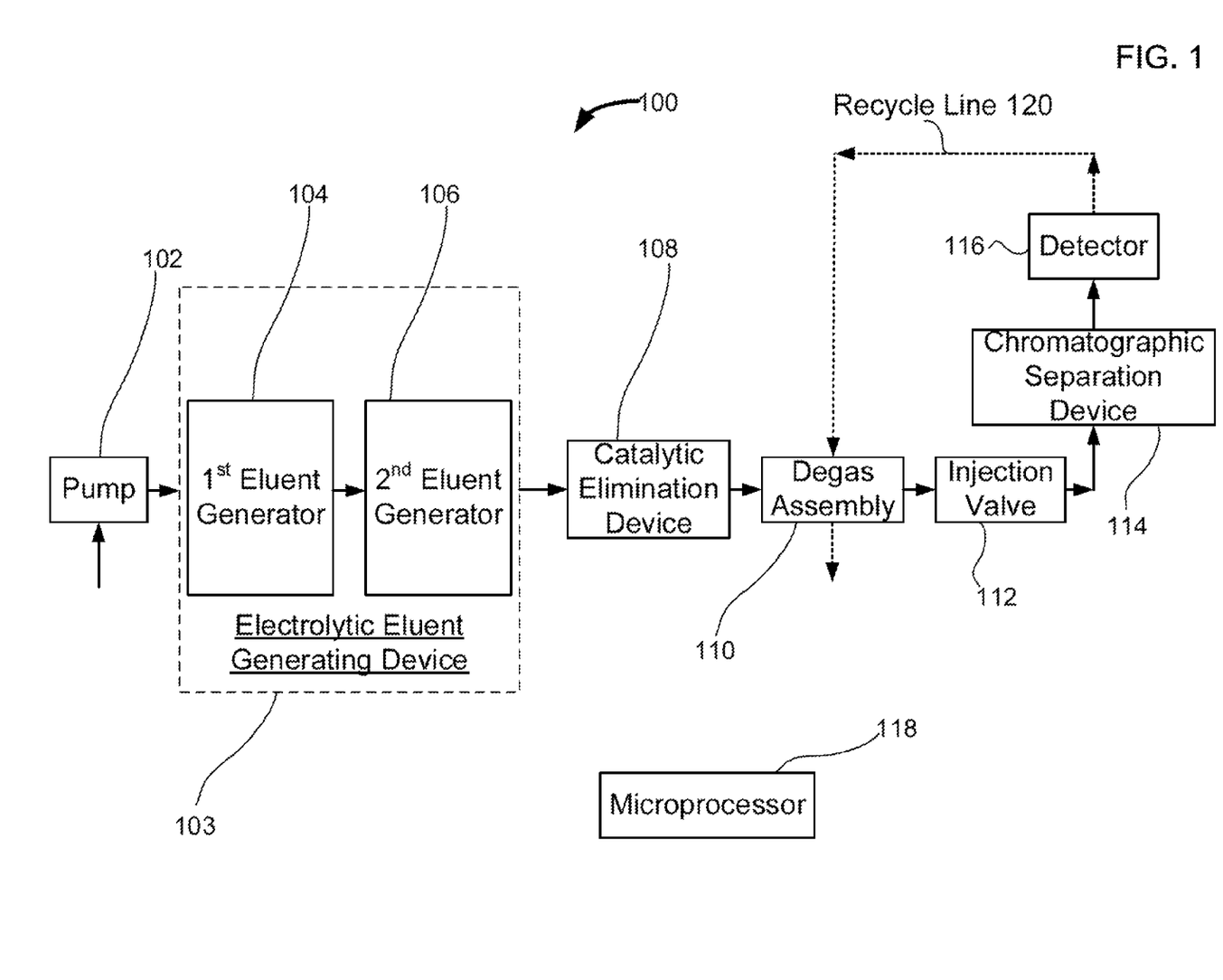
FIG. 1 illustrates an embodiment of a chromatography system that includes two eluent generators connected in series.

FIG. 1 illustrates an embodiment of a chromatography system 100 that includes two eluent generators (104 and 106) connected in series. Chromatography system 100 may include a pump 102, an electrolytic eluent generating device 103, a catalytic elimination device 108, a degas assembly 110, an injection valve 112, a chromatographic separation device 114, a detector 116, and a microprocessor 118. Chromatographic separation device 114 may be in the form of a capillary column. A recycle line 120 may be used to transfer the liquid from an output of detector 116 to an inlet of degas assembly 110.

Pump 102 can be configured to pump a liquid from a liquid source and be fluidically connected to electrolytic eluent generating device 103. In an embodiment, the liquid may be deionized water, an aqueous solution with electrolyte(s), or a mixture of an organic solvent with deionized water or with aqueous electrolyte(s) solution. A few example electrolytes are sodium acetate and acetic acid. The eluent mixture that contains an organic solvent may include a water miscible organic solvent such as, for example, methanol. Pump 102 can be configured to transport the liquid at a pressure ranging from about 20 PSI to about 6000 PSI. Under certain circumstances, pressures greater than 6000 PSI may also be implemented. It should be noted that the pressures denoted herein are listed relative to an ambient pressure (13.7 PSI to 15.2 PSI). Pump 102 may be in the form of a high pressure liquid chromatography (HPLC) pump. In addition, pump 102 can also be configured so that the liquid only touches an inert portion of pump 102 so that a significant amount of impurities does not leach out. In this context, significant means an amount of impurities that would interfere with the intended measurement. For example, the inert portion can be made of polyetherether ketone (PEEK) or at least coated with a PEEK lining, which does not leach out a significant amount of ions when exposed to a liquid.

Electrolytic eluent generating device 103 may include a first eluent generator 104 and a second eluent generator 106. An eluent is a liquid that contains an acid, base, salt, or mixture thereof and can be used to elute an analyte through a chromatography column. In addition, an eluent can include a mixture of a liquid and a water miscible organic solvent, where the liquid may include an acid, base, salt, or combination thereof. Electrolytic eluent generating device 103 is configured to generate two different generants where a first generant concentration and a second generant concentration are both controllable as a function of time. A generant refers to a particular species of acid, base, or salt that can be added to the eluent. In an embodiment, the first generant may be a base such as cation hydroxide and the second generant may be an acid such as carbonic acid, phosphoric acid, acetic acid, methanesulfonic acid, or a combination thereof.

Referring to FIG. 1, first eluent generator 104 can be configured to receive the liquid from pump 102 and then add a first generant to the liquid. A first gas byproduct may also be added to the liquid. Next, the liquid containing the first generant and the first gas byproduct can be outputted from first eluent generator 104.

Referring again to FIG. 1, second eluent generator 106 can be configured to receive the liquid from first eluent generator 104. A second generant and a second gas byproduct may be added to the liquid by second eluent generator 106. The liquid now contains the first generant, the second generant, the first gas byproduct, and the second gas byproduct. Next, the liquid can be outputted from second eluent generator 106 to an inlet of catalytic elimination device 108.

Catalytic elimination device 108 is configured to remove gases through a catalytic reaction. Catalytic elimination device 108 may include a catalyst such as, for example, platinum or other materials capable of combining hydrogen and oxygen into water and decomposing hydrogen peroxide and ozone. In an embodiment, an inert substrate can be coated with the catalyst. The catalyst can cause a first gas byproduct and a second gas byproduct to react and form water. In such a situation, hydrogen gas and oxygen gas may be the two gas byproducts. In addition, catalytic elimination device 108 can also be configured to decompose hydrogen peroxide byproduct, which can be beneficial for certain circumstances where hydrogen peroxide is present in the liquid. After catalytically reacting the first and second gas byproducts and/or decomposing hydrogen peroxide in the liquid, the liquid can be outputted to degas assembly 110. Details regarding catalytic elimination devices can be found in U.S. Pat. Nos. 7,329,346 and 8,043,507, which are hereby incorporated by reference herein.

Degas assembly 110 may be used to remove residual gas that is not removed by catalytic elimination device 108. In an embodiment, a residual gas may be carbon dioxide, hydrogen, and oxygen. Degas assembly 110 may include a tubing section that is gas permeable and liquid impermeable such as, for example, amorphous fluoropolymers or more specifically Teflon AF. The flowing liquid can be outputted from degas assembly 110 to injection valve 112 with a substantial portion of the gas removed. The gas can be swept out of degas assembly 110 using a recycled liquid via a recycle line 120 that is downstream of detector 116. The recycled liquid containing the residual gas can also be outputted from degas assembly 110 and directed to a waste container.

Injection valve 112 can be used to inject a bolus of a liquid sample into an eluent stream. The liquid sample may include a plurality of chemical constituents (i.e., matrix components) and one or more analytes of interest. Sample injection valve 112 will typically have two positions. In the first position, eluent will simply flow through injection valve 112 to chromatographic separation device 114. A user can load a liquid sample into a sample loop in injection valve 112 that has a predetermined volume. Once injection valve 112 is switched to the second position, eluent will flow through the sample loop and then introduce the liquid sample to chromatographic separation device 114. In an embodiment, injection valve 112 can be in the form of a six port valve.

Chromatographic separation device 114 can be used to separate various matrix components present in the liquid sample from the analyte(s) of interest. Typically, chromatographic separation device 114 may be in the form of a hollow cylinder that contains a packed stationary phase. As the liquid sample flows through chromatographic separation device 114, the matrix components and target analytes can have a range of retention times for eluting off of chromatographic separation device 114. Depending on the characteristics of the target analytes and matrix components, they can have different affinities to the stationary phase in chromatographic separation device 114. An output of chromatographic separation device 114 can be fluidically connected to detector 116 to measure the presence of the separated chemical constituents of the liquid sample.

As illustrated in FIG. 1, the fluidic output of the eluent from detector 116 is recycled to degas assembly 110 via recycle line 120. Detector 116 may be in the form of ultraviolet-visible spectrometer, a fluorescence spectrometer, an electrochemical detector, a conductometric detector, a charge detector, or a combination thereof. Details regarding the charge detector that is based on a charged barrier and two electrodes can be found in US Pre-Grant Publication No. 20090218238, which is hereby fully incorporated by reference herein. For the situation where recycle line 120 is not needed, detector 116 may also be in the form of a mass spectrometer or a charged aerosol detector. The charged aerosol detector nebulizes the effluent flow and creates charged particles that can be measured as a current proportional to the analyte concentration. Details regarding the charged aerosol detector can be found in U.S. Pat. Nos. 6,544,484; and 6,568,245, which are hereby fully incorporated by reference herein.

An electronic circuit may include microprocessor 118, a timer, and a memory portion. In addition, the electronic circuit may include a first and second power supplies that are configured to apply a first and second controlling signals, respectively. Microprocessor 118 can be used to control the operation of chromatography system 100. Microprocessor 118 may either be integrated into chromatography system 100 or be part of a personal computer that communicates with chromatography system 100. Microprocessor 118 may be configured to communicate with and control one or more components of chromatography system such as pump 102, first eluent generator 104, second eluent generator 106, injection valve 112, and detector 116. In an embodiment, microprocessor 118 can control a power supply that applies a first controlling signal to a first eluent generator 104 and a second controlling signal to a second eluent generator 106. The first and second controlling signal can be either a current or a voltage. The timer can be used to control and measure a duration of the current waveforms applied to first eluent generator 104 and second eluent generator 106. The memory portion may be used to store instructions to set the magnitude and timing of the current waveform with respect to the switching of injection valve 112 that injects the sample.

Figure 2:
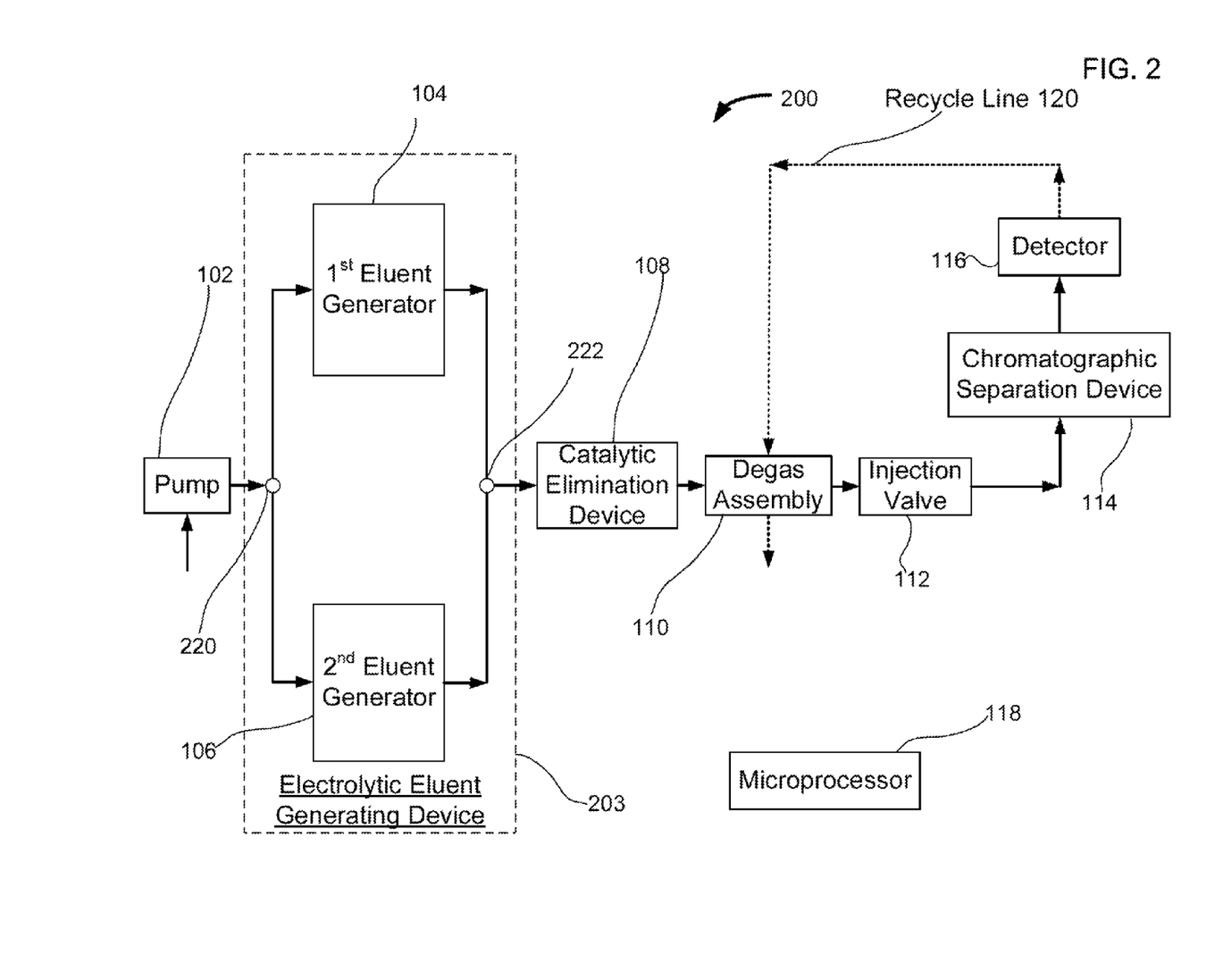
FIG. 2 illustrates an embodiment of a chromatography system that includes two eluent generators connected in parallel.

FIG. 2 illustrates an embodiment of a chromatography system 200 that includes two eluent generators connected in parallel. This is in contrast to chromatography system 100 that is configured in a serial format. In the parallel format, electrolytic eluent generating device 203 includes first eluent generator 104, second eluent generator 106, a first fluid junction 220, and a second fluid junction 222. Pump 102 can be configured to pump a liquid from a liquid source to both first eluent generator 104 and second eluent generator 106. A first fluid junction 220 can split the eluent flow to first eluent generator 104 and second eluent generator 106. A second fluid junction 222 can combine the eluent output of both first eluent generator 104 and second eluent generator 106. Second fluid junction may be in the form of a tee junction. Second fluid junction 222 can include a first inlet, a second inlet, and an outlet. The first inlet is configured to receive the liquid from first eluent generator 104. The second inlet is configured to receive the liquid from the second eluent generator 106. The two inputs can then be combined at fluid junction 222 to form a mixture. The outlet is configured to flow the mixture of the first generant, the second generant, the first gas byproduct, and the second gas byproduct. The mixture can then be outputted to chromatographic separation device 114 via catalytic elimination device 108, degas assembly 110, and injection valve 112.

The parallel format of eluent generating device 203 can provide more flexibility in independently modifying the generation chamber of either of the two eluent generators. For example, the following characteristics may be modified for one the eluent generators such as the volume of generation chamber, the bore size of the inlet and outlet tubing of the fluid junctions, the area of the ion exchange barrier in fluidic contact with the flowing liquid carrier, and the area of the electrode. Such changes can modify the ratio of the two generant concentrations at a particular flow rate.

In an embodiment similar to chromatography system 200 (not shown), two pumps may be used to deliver different liquids to the first eluent generator 104 and the second eluent generator 106 independently. In this embodiment, the first fluid junction 220 is not used.

Figure 3:
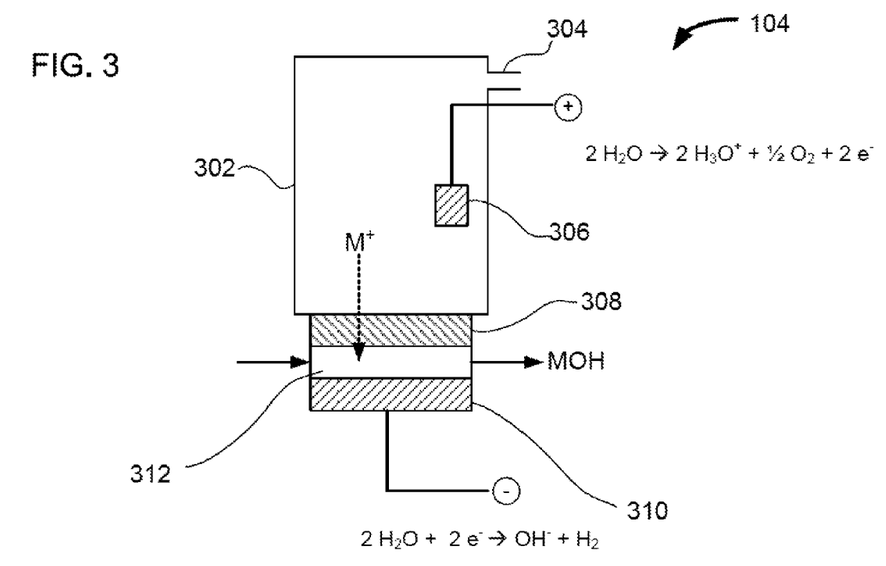
FIG. 3 illustrates an embodiment of a 1$^{st}$ eluent generator configured to generate a cation hydroxide.

Now that chromatography systems 100 and 200 have been described, the following will describe, in more detail, the structure of first eluent generator 104 and second eluent generator 106. Referring to FIG. 3, first eluent generator 104 includes a first ion source reservoir 302, a vent 304, a first generation chamber 312, a first ion exchange barrier 308, a first electrode 306, and a second electrode 310. First ion source reservoir 302 can include a source of cations or anions. First generation chamber 312 can include an inlet configured to receive the liquid and an outlet configured to output the liquid that includes the first generant and the first gas byproduct. First ion exchange barrier 308 can be at least partly disposed between first ion source reservoir 302 and first generation chamber 312. First electrode 306 is in electrical communication with the first ion source reservoir 302. Second electrode 310 is in electrical communication with the first generation chamber 312.

As illustrated in FIG. 3, first eluent generator 104 is configured to generate a cation hydroxide eluent (MOH). First ion source reservoir 302 may include a solution containing KOH, NaOH, LiOH, ammonium hydroxide, salts of alkali metal ions, and other organic and inorganic cations commonly used in the eluents for liquid chromatography and ion chromatography. In an embodiment, first ion source reservoir 302 may have a relatively low pressure such as, for example, about atmospheric pressure. First electrode 306 is connected to a positive polarity pole of a current supply and second electrode 310 is connected to a negative polarity pole of the current supply. In this format, first electrode 306 is referred to as an anode where an oxidation reaction can occur. Water can be oxidized at the anode disposed in first ion source reservoir 302 to form hydronium ions and an oxygen gas byproduct.

Second electrode 310 is referred to as a cathode where a reduction reaction can occur. When a current is applied, water can be reduced at the cathode disposed in first generation chamber 312 to form hydroxide ions and a hydrogen gas byproduct. In an embodiment, first generation chamber 312 may have a relatively high pressure ranging from about 20 PSI to about 6000 PSI. Under certain circumstances, pressures greater than 6000 PSI may also be implemented. First and second electrodes may be an inert conductive material such as, for example, palladium, platinum, iridium, or a combination thereof.

First ion exchange barrier 308 may be in the form of a cation exchange membrane. The cation exchange membrane can be charged with cations such as sodium or potassium from the first ion source reservoir 302. The cation exchange barrier is configured to allow cations to flow through, but block the bulk flow of liquid. Under the applied electrical field, cations in the first ion source reservoir 302 migrate across the cation exchange membrane and combine with hydroxide ions generated at the cathode 310 to form cation hydroxide. An example of a cation exchange membrane includes the CMI-7000 cation exchange membrane manufactured by Membrane International Inc. (Ringwood, N.J.). In one embodiment, the electrolyte solution present in first ion source reservoir 302 may include a weakly basic anion to bind hydronium ions so as to prevent the hydronium ions from diffusing through the cation exchange membrane. In summary, the liquid entering first generation chamber 312 is mixed with a cation $M^+$ (e.g., sodium or potassium) from first ion source reservoir 302 and hydroxide generated at second electrode 310 to form a cation hydroxide solution (MOH).

Figure 4:
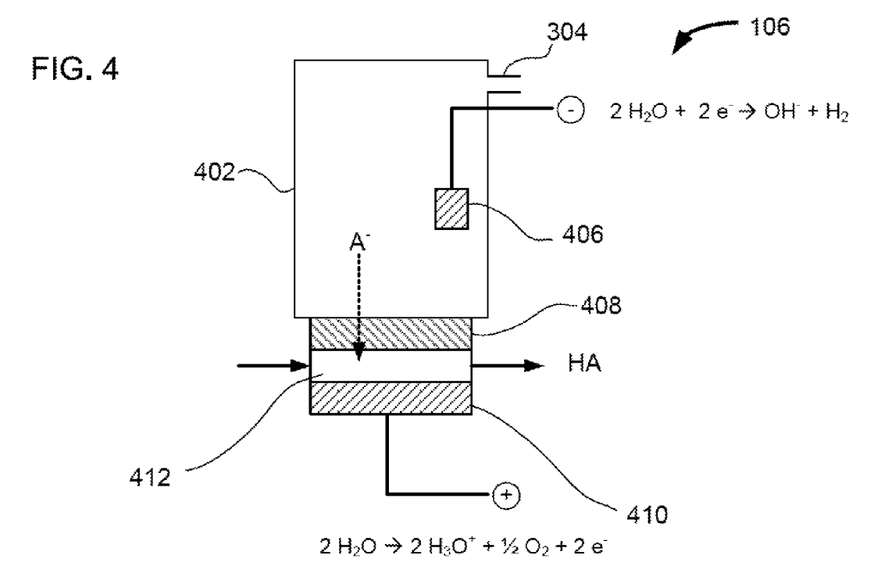
FIG. 4 illustrates an embodiment of a 2$^{nd}$ eluent generator configured to generate an acid.

Referring to FIG. 4, second eluent generator 106 includes a second ion source reservoir 402, a vent 304, a second generation chamber 412, a second ion exchange barrier 408, a third electrode 406, and a fourth electrode 410. Second ion source reservoir 402 can include a source of cations or anions. Second generation chamber 412 can include an inlet configured to receive the liquid and an outlet configured to output the liquid that includes the second generant and the second gas byproduct. Second ion exchange barrier 408 can be at least partly disposed between second ion source reservoir 402 and second generation chamber 412. Third electrode 406 is in electrical communication with the second ion source reservoir 402. Fourth electrode 410 is in electrical communication with the second generation chamber 412.

As illustrated in FIG. 4, second eluent generator 106 is configured to generate an acid eluent. Second eluent generator 106 is similar to first eluent generator 104 except that the polarity of the applied current and the charge of the ion exchange barrier are reversed. Second ion source reservoir 402 may include a solution containing methanesulfonic acid, sulfuric acid, phosphoric acid, trifluoroacetic acid, acetic acid, or other organic and inorganic acids commonly used in eluents for liquid chromatography and ion chromatography, or a combination thereof. In an embodiment, second ion source reservoir 402 may have a relatively low pressure such as, for example, about atmospheric pressure. Third electrode 406 is connected to a negative polarity pole of a current supply and fourth electrode 410 is connected to a positive polarity pole of the current supply. In this format, third electrode 406 is referred to as a cathode where a reduction reaction can occur. Water can be reduced at the cathode disposed in second ion source reservoir 402 to form hydroxide ions and a hydrogen gas byproduct.

Fourth electrode 410 is referred to as an anode where an oxidation reaction can occur. When a current is applied, water can be oxidized at the anode disposed in second generation chamber 412 to form hydronium ions and an oxygen gas byproduct. In an embodiment, first generation chamber 312 may have a relatively high pressure ranging from about 20 PSI to about 6000 PSI. First and second electrodes may be an inert conductive material such as, for example palladium, platinum, iridium, or a combination thereof.

Second ion exchange barrier 408 may be in the form of an anion exchange membrane. The anion exchange membrane can be charged with anions such as carbonate, methanesulfonate, acetate, or phosphate from the second ion source reservoir 402. The anion exchange barrier is configured to allow anions to flow through, but block the bulk flow of liquid. Under the applied electrical field, the anions ($A^-$) in the first ion source reservoir 402 migrate across anion exchange membrane and combine with hydronium ions generated at the anode 410 to form an acid (HA) solution. An example of an anion exchange membrane includes the AMI-7000 anion exchange membrane manufactured by Membrane International Inc. (Ringwood, N.J.). In one embodiment, the electrolyte solution present in second ion source reservoir 402 may contain a weakly acidic cation to bind hydroxide ions so as to prevent the hydroxide ions from diffusing through the anion exchange membrane. In summary, the liquid entering second generation chamber 412 is mixed with an anion $A^-$ from second ion source reservoir 402 and hydronium generated at fourth electrode 410 to form an acidic HA solution.

As an example, the first generant can be KOH and the second generant can be methanesulfonic acid (MSA). In this example, the KOH can react with the MSA to form a solution of the potassium salt (i.e., potassium methanesulfonate (KMSA)). It should be noted that although the embodiments described herein illustrate only two eluent generators, embodiments can also be made with more than two eluent generators. Further, the embodiments described herein illustrate a first base generator and a second acid generator, the embodiments can also be made with a different sequential order of acid and base generators. Yet further, the embodiments can also be made with only acid generators or with only base generators.

It should be noted that the electrolytic eluent generating devices described herein may be configured to generate as an output two different anionic species such as $MSA^-$ and $OH^-$ because of the use of one or more power supplies that can apply more than one controlling signal. In these embodiments, a first generant and a second generant can be selected that do not share a common anion. As a result, a user can now select from a wide range of eluent combinations and apply a wide range of time dependent concentration profiles that were heretofore unavailable for performing capillary ion chromatography separations.

Now that embodiments of multi-component eluent generating devices have been described, the following will describe methods of using such devices. A method of generating a concentration gradient eluent flow with at least two generants includes pumping a liquid to an electrolytic eluent generating device (103 or 203). A first controlling signal can be applied to first eluent generator 104 to generate a first generant concentration. After applying the first controlling signal, first eluent generator 104 can generate a first generant and a first gas byproduct, which is then added to the liquid. The first generant concentration produced by the electrolytic eluent generating device can be directly proportional to a magnitude of the applied current and inversely proportional to the flow rate of the carrier stream. A second controlling signal can be applied to a second eluent generator 106 to generate a second generant concentration. After applying the second controlling signal, second eluent generator 106 can generate a second generant and a second gas byproduct, which is then added to the liquid. The second generant concentration produced by the electrolytic eluent generating device can be directly proportional to a magnitude of the applied current and inversely proportional to the flow rate of the carrier stream. The first and second controlling signal can be a first and second current, respectively. Either the first or second controlling signal can be increased or decreased as a function of time to generate a concentration gradient flow. In another embodiment, both the first and second controlling signals can be increased or decreased as a function of time to generate a concentration gradient flow.

Once the electrolytic eluent generating device 103 has produced a liquid that contains the first and second generant, catalytic elimination device 108 can remove the first and second gas byproducts by catalyzing a reaction that forms water. A liquid sample that includes an analyte can be injected into an inlet of chromatographic separation device 114. Next, the eluent or liquid, that includes the first and second generant, can be inputted into chromatographic separation device 114 and provide a concentration gradient eluent flow. The target analytes can separate from the matrix components and from each other in chromatographic separation device 114. In this situation, the matrix components and analyte(s) will elute off of chromatographic separation device 114 during a range of elution times and then be detected with detector 116.

The first and/or the second controlling signal can be increased as a function of time to generate a concentration gradient eluent flow. In an embodiment, one controlling signal can be varied as a function of time and the other controlling signal can be held to be approximately constant. In addition, the current waveform can include one or more current steps where the applied current has an approximately constant first predetermined magnitude for a first time duration followed by a switch to an approximately constant second predetermined magnitude for a second time duration. The first predetermined magnitude may be less than or greater than the second predetermined magnitude. The current waveform can include one or more linear ramps where the applied current can increase or decrease in a linear manner for a predetermined time duration. It should also be noted that the current waveform can be a combination of current steps and linear or curved current ramps.

In an embodiment, microprocessor 118 can apply a first controlling signal to the first eluent generator 104 to control the first generant concentration. In addition, microprocessor 118 can apply a second controlling signal to the second eluent generator 106 to control the second generant concentration. The first or second controlling signals can independently be increased or decreased as a function of time to generate a concentration gradient eluent flow. The first controlling signal may be a first current or a first voltage. Similarly, the second controlling signal may be a second current or a second voltage. Microprocessor 118 can also be configured to synchronize an actuation of injection valve 112 so that at least a portion of a concentration gradient eluent flow elutes the analyte on chromatographic separation device 114. The controlling signal waveforms can be initiated during a chromatographic run either before or after the sample is injected. A cycle or duration of the waveform should have a time duration that is about the same or longer than the retention time of the analyte. In addition, microprocessor 118 can control the flow rate, pressure, and duration of the liquid eluent flow of pump 102.

In regards to chromatography system 100 of FIG. 1, the liquid output from the first eluent generator 104 is inputted into an inlet of the second eluent generator 106. The output of the second eluent generators 106 will contain the combination of the first and second generants and the first and second gas byproducts. Thus, the adding of the second generant is to a liquid that already contains the first generant. It should be pointed out that the order of producing generants in chromatography system 100 can be important in providing reproducible chromatograms where the peak retention times have relatively low levels of variation. When using the serial format of FIG. 1, it is preferred that the second eluent generator 106 produces the generant with stronger elution capabilities so that the concentration can be precisely controlled with a shorter delay effect. For example, methanesulfonate has stronger eluting capability than hydroxide ions. In one embodiment, a MSA eluent generator is used as the second eluent generator 106 and a KOH eluent generator is used as the first eluent generator 104. Note that the shorter delay effects can result because second eluent generator 106 is closer to chromatographic separation device 114. Stronger eluting capability refers to a generant that elutes that analyte off of the chromatographic separation device with a shorter retention time. The liquid source that is inputted into the first eluent generator 104 (upstream portion of electrolytic eluent generating device 103) has an approximately constant chemical composition. For example, the liquid source can be deionized water. As such, the applied current to first eluent generator 104 can output a reproducible concentration of first generant as a function of time. In contrast, the ionic strength of the liquid inputted into the second eluent generator 106 (downstream portion of electrolytic eluent generating device 103) can have a dynamic ionic strength. The second generation chamber of the second eluent generator 106 may have a lower resistance than the first generation chamber of the first eluent generator 104. Therefore, one unexpected benefit is that the second generation chamber can conduct more current due to the lower liquid resistance, and thus, can generate higher generant concentrations than the situation where deionized water is inputted into first generation chamber 312. In an embodiment, the KOH concentration may range from about 0 mM to about 200 mM, and preferably range from about 0 mM to about 1000 mM. The MSA concentration may range from about 0 mM to about 200 mM, and preferably range from about 0 mM to about 1000 mM.

Multi-component eluent generating devices described herein are well-suited to do capillary-scale concentration gradient separations because of the low dead volume, relatively short delay times, low carbon dioxide contamination, and low heat effects. The multi-component eluent generators described herein have relatively low dead volumes because they do not require mechanical proportioning devices that are connected to a pump. The dead volume of the eluent generating devices described herein is based essentially on the geometric dimensions of the generation chambers (312 and 412). Thus, the dead volume may range from about 1 microliter to about 100 microliters. In turn, the relatively low dead volumes allow the eluent concentration to be changed relatively quickly causing the delay time to be relatively short too.

It should also be noted that multi-component eluent generators described herein create carbonate-free generants in situ, and thus, prevents carbon dioxide from interfering with the analysis. Under certain circumstances, the storage of basic generants in a reservoir for a prolonged period of time can be difficult to do because carbon dioxide from ambient air reacts with the basic generant to form carbonate which can interfere with chromatographic separations. Creating the generants in situ immediately before use reduces the risk of carbon dioxide contamination. Capillary chromatography is especially susceptible to carbon dioxide contamination because of the low eluent flow rates. The multi-component eluent generators described herein with in situ generation allow concentration gradient eluent delivery with reduced carbonate contamination.

Under certain circumstances, heat generation by an eluent generator can interfere with the chromatographic separations. The use of multiple electrolytic eluent generators can exacerbate the generation of heat. This heat generation is a result of joule heating caused by the application of an electrical current across a fluid. Surprisingly, applicants found that the use of two eluent generators did not cause significant heating to the eluent when applied to capillary chromatography. Applicant believes that the relatively high surface area to volume ratio in the chromatography system allow the heat to dissipate efficiently. In addition, applicant believes that that the wattage for the capillary eluent generators is substantially lower than macro eluent generators that are used with columns having an internal diameter of 2 to 4 mm. The wattage of an electrolytic eluent generator is proportional to $I^2R$ where I=the applied current and R=the resistance. The resistance R is the same for the capillary and macro eluent generators if the spacing between the membrane and electrode is about the same. The current I is much lower for the capillary eluent generator because the eluent flow rate and the amount of generant are significantly lower than the macro eluent generator. Note that the smaller volume of the capillary system causes the amount of generant to be relatively low. Thus, the wattage is substantially decreased for the capillary situation because the current I is a squared term and causes much less heat to be generated.

EXAMPLE 1

A chromatography system was constructed in a format similar to FIG. 1. A Thermo Scientific Dionex capillary EGC KOH cartridge was used for first eluent generator 104 and a Thermo Scientific Dionex capillary EGC MSA cartridge was used for second eluent generator 106 (Thermo Fisher Scientific, Sunnyvale, Calif.). Two catalytic elimination devices were prepared by inserting a 0.010 inch outer diameter (OD) Pt wire into a 250 mm×0.015-inch PEEK tubing. Two 10-32 PEEK couplers were used to fabricate the inlet and outlet of the Pt catalyst columns. One catalytic elimination device was placed at the outlet of the capillary EGC KOH cartridge (not shown) and the other catalytic elimination device 108 was placed at the outlet of the capillary EGC MSA cartridge. A Thermo Scientific capillary CarboPac PA20 column (0.4 mm ID×150 mm length) was used as the chromatographic separation device 114. The detector 116 was a Thermo Scientific electrochemical detector fitted with Au electrodes. The experimental system was used in the determination of sialic acids and inulins.

EXAMPLE 2

Figure 5:
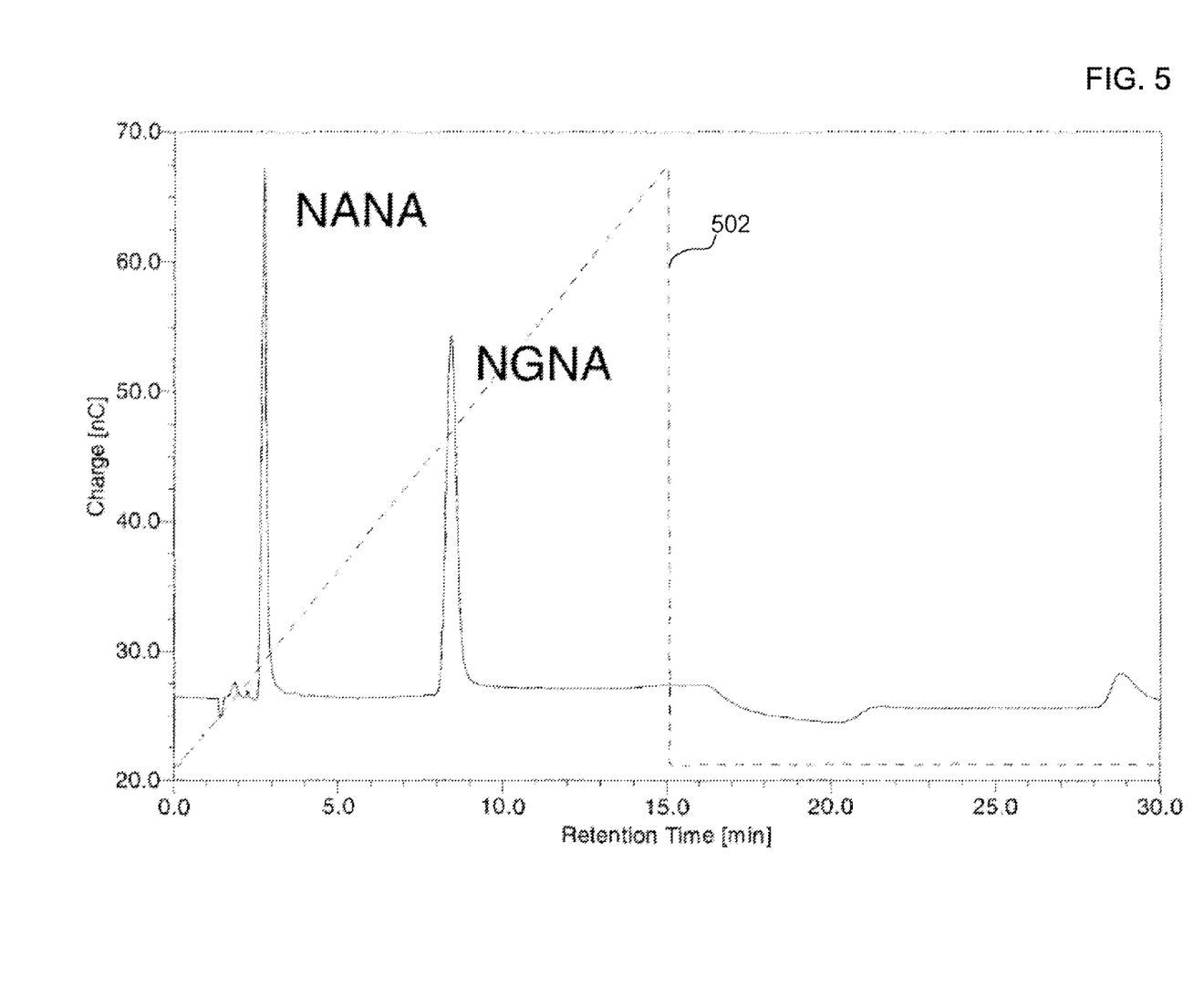
FIG. 5 shows a chromatogram of a concentration gradient separation of sialic acids on a capillary column.

An experiment was performed to show that sialic acids such as N-acetylneuraminic acid (NANA) and N-glycolylneuraminic acid (NGNA) could be separated using electrolytic eluent generating device 103. FIG. 5 shows the concentration gradient separation of sialic acids on a capillary CarboPac PA20 column at 30° C. and 8 µL/min. 0.4-uL samples containing 27 µM NANA and 22 µM NGNA were analyzed. The electrochemical detector was fitted with a Thermo Scientific Dionex disposable PTFE Au electrode and operated in the integrated pulsed amperometric mode using a quadruple waveform. Table 1 shows the applied potentials and time durations of the quadruple waveform.

TABLE 1

| Time (s) | Potential (V) | Integration |
|---|---|---|
| 0.00 | 0.10 | |
| 0.20 | 0.10 | Start |
| 0.40 | 0.10 | End |
| 0.41 | −2.00 | |
| 0.42 | −2.00 | |
| 0.43 | 0.60 | |
| 0.44 | −0.10 | |
| 0.50 | −0.10 | |

In this separation, the capillary EGC KOH was controlled to produce 180 mM KOH constantly. During the same time period, the capillary EGC MSA cartridge was controlled to produce 10 to 60 mM MSA from 0 to 15 minutes as illustrated by a current-time trace 502 of FIG. 5. Therefore, the composition of the eluent going into the chromatographic separation column was varied from 170 mM KOH and 10 mM KMSA at the beginning of the run to 120 mM KOH and 60 mM KMSA at 15 minutes. It should be noted that the net output of the electrolytic eluent generating device was a concentration gradient that included a decreasing concentration gradient of hydroxide anions and an increasing concentration gradient of potassium methanesulfonate at the same time. Under the concentration gradient condition used, NANA is eluted before NGNA as shown in FIG. 5. By using increasing KMSA concentration in the eluent under the concentration gradient condition used, it was possible to obtain fast elution of NANA and NGNA from the capillary Dionex CarboPac PA20 column in less than 10 minutes. This was a surprising result because the pH changed as a function of time with this concentration gradient. Previously, a changing pH would typically cause an unstable baseline when using an electrochemical detector. However, the baseline in this example was observed to be relatively stable, as illustrated in FIG. 5. In addition, applicants believe that the decreasing pH values as a function of time, along with the two component concentration gradients, caused the sialic acid analytes to elute in a faster time frame with sufficient resolution than previously observed in other chromatographic separations. As the pH values decreased, the proportion of anionic sites on the sialic acids decreased, which in turn decreased the affinity to the stationary phase.

EXAMPLE 3

Figure 6:
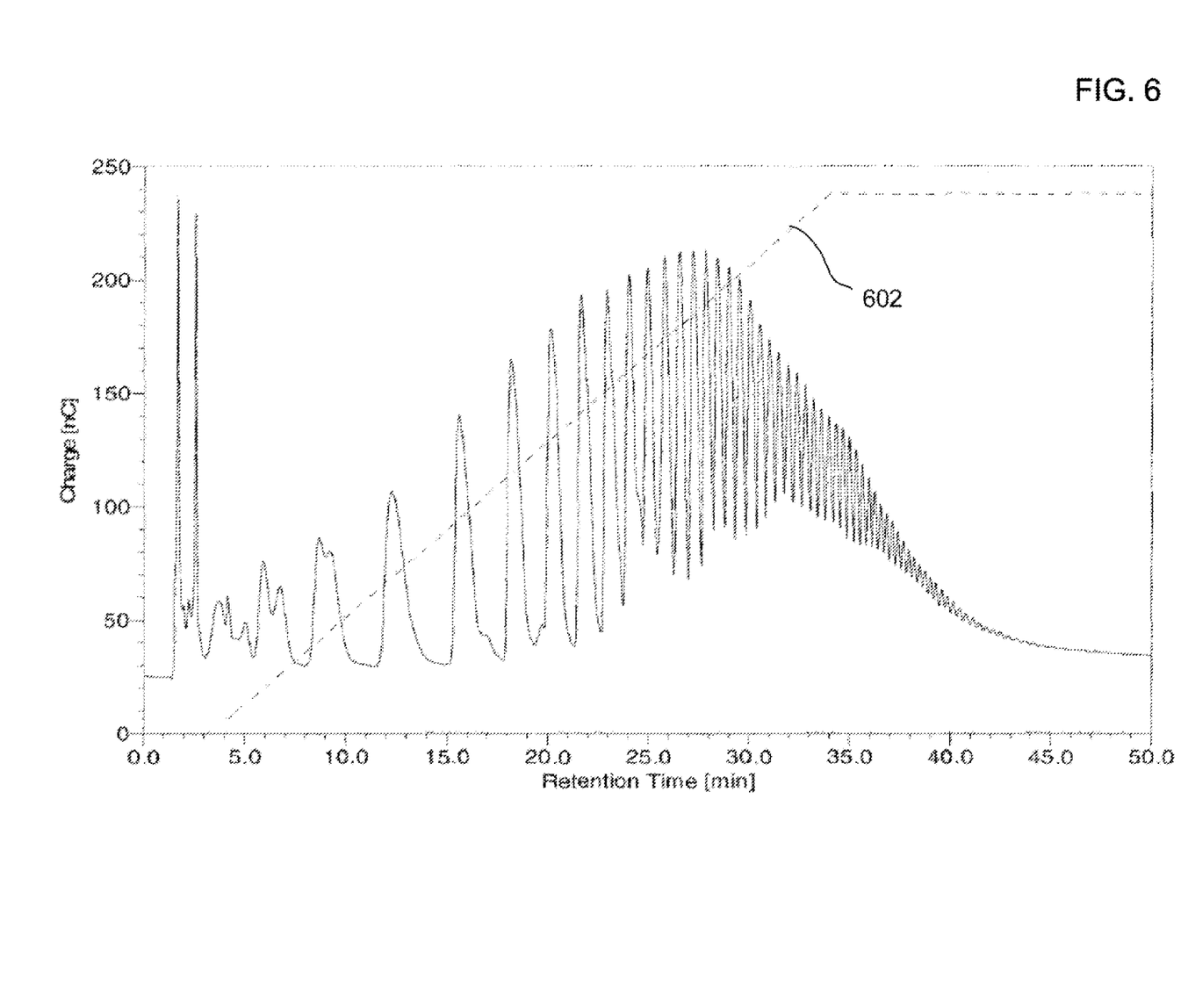
FIG. 6 shows a chromatogram of a concentration gradient separation of inulin oligosaccharides on a capillary column.

An experiment was performed to show that inulins could be separated using electrolytic eluent generating device 103.

FIG. 6 shows the concentration gradient separation of inulins, which are a group of naturally occurring polysaccharides on a capillary CarboPac PA20 column at 30° C. and 8 µL/min. 0.4-uL samples containing 56 mg of inulins were analyzed. The electrochemical detector was fitted with a Thermo Scientific Dionex disposable PTFE Au electrode and operated in the integrated pulsed amperometric mode using the standard quadruple waveform. In this separation, the capillary EGC KOH was controlled to produce 180 mM KOH constantly. During the same time period, the capillary EGC MSA cartridge was controlled to produce 55 to 140 mM MSA from 0 to 35 minutes and 140 mM MSA from 35 to 50 minutes, as illustrated by a current-time trace 602 of FIG. 6. Therefore, the composition of the eluent going into the separation column was varied from 125 mM KOH and 55 mM KMSA at the beginning of the run to 50 mM KOH and 140 mM KMSA at 35 to 50 minutes. Under the concentration gradient condition used, good resolution of inulin oligomers was achieved.

EXAMPLE 4

Figure 7:
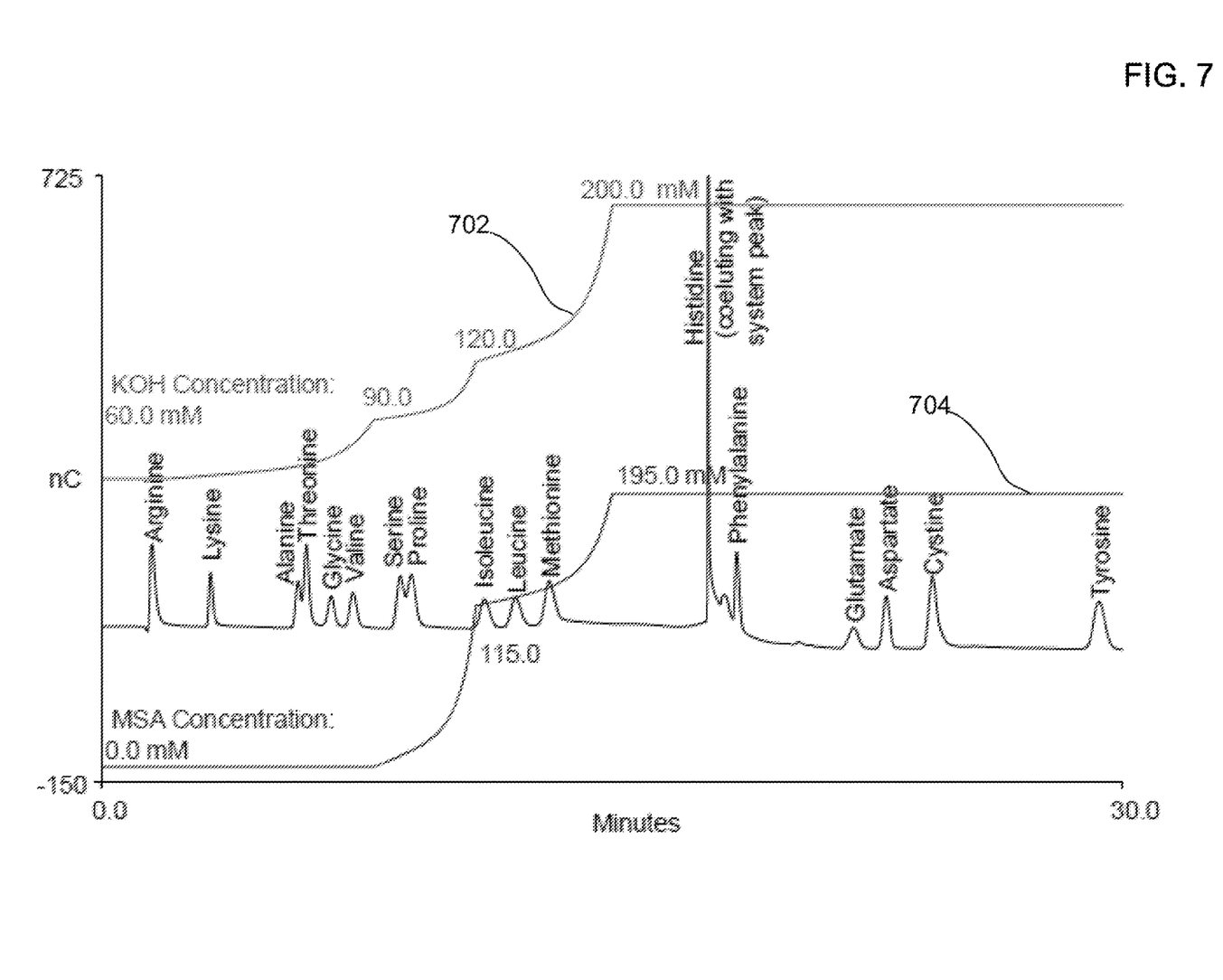
FIG. 7 shows a chromatogram of a concentration gradient separation of 17 hydrolysate amino acids on a capillary column.

An experiment was performed to show a concentration gradient separation of 17 hydrolysate amino acids on a prototype capillary Dionex AminoPac PA10 column using electrolytic eluent generating device 203. The concentration gradient separation of hydrolysate amino acids was obtained using chromatograph system with a similar format to system 200 of FIG. 2. In this case, the capillary Dionex EGC-MSA and EGC-KOH cartridges were pumped with deionized water independently. The KOH and MSA eluents formed were mixed via a tee before being directed into the separation column. The electrolytic eluent generation platform makes it possible to generate rather complex concentration gradient profiles of KOH and KMSA eluents to achieve the separation of 17 hydrolysate amino acids on a prototype capillary Dionex AminoPac PA10 column as shown in FIG. 7. The KOH and KMSA current-time traces are illustrated as 702 and 704, respectively, in FIG. 7.

While preferred embodiments of the present invention have been shown and described herein, it will be apparent to those skilled in the art that such embodiments are provided by way of example only. Numerous variations, changes, and substitutions will now occur to those skilled in the art without departing from the invention. While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. An electrolytic eluent generating device configured to generate at least two different generants, in which the at least two different generants include a first generant and a second generant, where a first generant concentration and a second generant concentration are both controllable as a function of time, the electrolytic eluent generating device comprising;

a) a first eluent generator configured to
  i) receive a liquid from a pump;
  ii) add the first generant to the liquid; and
  iii) output the liquid that includes the first generant, in which the first eluent generator comprises:
  iv) a first ion source reservoir including a source of cations or anions;
  v) a first generation chamber including an inlet configured to receive the liquid and an outlet configured to output the liquid that includes the first generant;
  vi) a first ion exchange barrier at least partly disposed between the first ion source reservoir and the first generation chamber;
  vii) a first electrode in electrical communication with the first ion source reservoir; and
  viii) a second electrode in electrical communication with the first generation chamber; and
b) a second eluent generator configured to
  i) receive the liquid from the first eluent generator;
  ii) add the second generant to the liquid; and
  iii) output the liquid that includes the first generant and the second generant, in which the second eluent generator comprises:
  iv) a second ion source reservoir including a source of cations or anions;
  v) a second generation chamber including an inlet configured to receive the liquid from the first eluent generator and an outlet configured to output the liquid that includes the first generant and the second generant;
  vi) a second ion exchange barrier at least partly disposed between the second ion source reservoir and the second generation chamber;
  vii) a third electrode in electrical communication with the second ion source reservoir; and
  vii) a fourth electrode in electrical communication with the second generation chamber,
in which the first and second eluent generators together have a dead volume ranging from about 1 microliter to about 100 microliters.

2. The electrolytic eluent generating device of claim 1, in which the dead volume is a sum of a first volume of the first generation chamber and a second volume of the second generation chamber.

3. The electrolytic eluent generating device of claim 1, in which the first generant is a compound comprising an anion and a cation, the anion selected from the group consisting of a hydroxide, a carbonate, a phosphate, a sulfate, a trifluoroacetate, an acetate, a methanesulfonate, and a combination thereof, the cation selected from the group consisting of a hydronium, a potassium, a sodium, a lithium, an ammonium, and a combination thereof.

4. The electrolytic eluent generating device of claim 1, in which the second generant is a compound comprising an anion and a cation, the anion selected from the group consisting of a hydroxide, a carbonate, a phosphate, a sulfate, a trifluoroacetate, an acetate, a methanesulfonate, and a combination thereof, the cation selected from the group consisting of a hydronium, a potassium, a sodium, a lithium, an ammonium, and a combination thereof.

5. The electrolytic eluent generating device of claim 1, in which the first generant and the second generant do not share a common anion.

6. The electrolytic eluent generating device of claim 1, in which the first ion exchange barrier and the second ion exchange barrier comprise a cation exchange membrane and an anion exchange membrane, respectively.

7. The electrolytic eluent generating device of claim 1, in which the first electrode is an anode disposed in the first ion source reservoir and the second electrode is a cathode disposed in the first generation chamber.

8. The electrolytic eluent generating device of claim 1, in which the third electrode is a cathode disposed in the second ion source reservoir and the fourth electrode is an anode disposed in the second generation chamber.

9. A method of generating a concentration gradient eluent flow, the method comprising:
   pumping a liquid into an electrolytic eluent generating device of claim 1;
   adding a first generant and a second generant to the liquid;
   injecting a liquid sample that includes an analyte into a chromatographic separation device;
   inputting the liquid that includes the first generant and the second generant to provide a concentration gradient eluent flow into the chromatographic separation device;
   separating the analyte from matrix components in the chromatographic separation device; and
   detecting the analyte with a detector.

10. An electrolytic eluent generating device configured to generate at least two different generants, in which the at least two different generants include a first generant and a second generant, where a first generant concentration and a second generant concentration are both controllable as a function of time, the electrolytic eluent generating device comprising;
   a) a first eluent generator configured to
      i) receive a liquid from a pump;
      ii) add the first generant to the liquid; and
      iii) output the liquid that includes the first generant, in which the first eluent generator comprises:
      iv) a first ion source reservoir including a source of cations or anions;
      v) a first generation chamber including an inlet configured to receive the liquid and an outlet configured to output the liquid that includes the first generant;
      vi) a first ion exchange barrier at least partly disposed between the first ion source reservoir and the first generation chamber;
      vii) a first electrode in electrical communication with the first ion source reservoir; and
      viii) a second electrode in electrical communication with the first generation chamber; and
   b) a second eluent generator configured to
      i) receive the liquid from the pump;
      ii) add the second generant to the liquid; and
      iii) output the liquid that includes the second generant, in which the second eluent generator comprises:
      iv) a second ion source reservoir including a source of cations or anions;
      v) a second generation chamber including an inlet configured to receive the liquid and an outlet configured to output the liquid that includes the second generant;
      vi) a second ion exchange barrier at least partly disposed between the second ion source reservoir and the second generation chamber;
      vii) a third electrode in electrical communication with the second ion source reservoir; and
      vii) a fourth electrode in electrical communication with the second generation chamber; and
   c) a fluid junction including a first inlet, a second inlet, and an outlet, where
      i) the first inlet is configured to receive the liquid from the first eluent generator;
      ii) the second inlet is configured to receive the liquid from the second eluent generator; and
      iii) the outlet is configured to flow a mixture of the first generant and the second generant,
   in which the first and second eluent generators together have a dead volume ranging from about 1 microliter to about 100 microliters.

11. The electrolytic eluent generating device of claim 10, in which the dead volume is a sum of a first volume of the first generation chamber and a second volume of the second generation chamber.

12. The electrolytic eluent generating device of claim 10, in which the first generant is a compound comprising an anion and a cation, the anion selected from the group consisting of a hydroxide, a carbonate, a phosphate, a sulfate, a trifluoroacetate, an acetate, a methanesulfonate, and a combination thereof, the cation selected from the group consisting of a hydronium, a potassium, a sodium, a lithium, an ammonium, and a combination thereof.

13. The electrolytic eluent generating device of claim 10, in which the second generant is a compound comprising an anion and a cation, the anion selected from the group consisting of a hydroxide, a carbonate, a phosphate, a sulfate, a trifluoroacetate, an acetate, a methanesulfonate, and a combination thereof, the cation selected from the group consisting of a hydronium, a potassium, a sodium, a lithium, an ammonium, and a combination thereof.

14. The electrolytic eluent generating device of claim 10, in which the first generant and the second generant do not share a common anion.

15. The electrolytic eluent generating device of claim 10, in which the first ion exchange barrier and the second ion exchange barrier comprise a cation exchange membrane and an anion exchange membrane, respectively.

16. The electrolytic eluent generating device of claim 10, in which the first electrode is an anode disposed in the first ion source reservoir and the second electrode is a cathode disposed in the first generation chamber.

17. The electrolytic eluent generating device of claim 10, in which the third electrode is a cathode disposed in the second ion source reservoir and the fourth electrode is an anode disposed in the second generation chamber.

* * * * *